United States Patent
Davenport

(10) Patent No.: US 6,378,520 B1
(45) Date of Patent: Apr. 30, 2002

(54) VARIABLE PRESSURE AND FLOW CONTROL FOR A PNEUMATICALLY-OPERATED GAS DEMAND APPARATUS

(75) Inventor: James M. Davenport, Fallbrook, CA (US)

(73) Assignee: Salter Labs, Arvin, CA (US)

( * ) Notice: Subject to any disclaimer, the term of this patent is extended or adjusted under 35 U.S.C. 154(b) by 0 days.

(21) Appl. No.: 09/430,547

(22) Filed: Oct. 29, 1999

(51) Int. Cl.⁷ .......... A61M 16/00; A62B 7/04; F16K 31/26
(52) U.S. Cl. .......... 128/204.26; 128/204.18; 128/204.23; 128/204.24; 128/205.24; 128/205.28
(58) Field of Search .......... 128/204.18, 204.23, 128/204.24, 204.26, 205.24, 207.18

(56) References Cited

U.S. PATENT DOCUMENTS

| | | | | |
|---|---|---|---|---|
| 4,232,668 A | * | 11/1980 | Strupat | 128/204.24 |
| 4,323,064 A | * | 4/1982 | Hoenig et al. | 128/204.21 |
| 4,686,974 A | * | 8/1987 | Sato et al. | 128/204.23 |
| 5,024,219 A | * | 6/1991 | Dietz | 128/204.21 |
| 5,307,795 A | * | 5/1994 | Whitwam et al. | 128/204.25 |
| 5,331,995 A | * | 7/1994 | Westfall et al. | 137/8 |
| 5,664,563 A | * | 9/1997 | Schroeder et al. | 128/204.25 |
| 5,666,945 A | | 9/1997 | Davenport | |
| 6,148,816 A | * | 11/2000 | Heinonen et al. | 128/205.24 |
| 6,155,256 A | * | 12/2000 | Wallin | 128/203.16 |
| 6,192,885 B1 | * | 2/2001 | Jalde | 128/205.24 |
| 6,213,120 B1 | * | 4/2001 | Block et al. | 128/204.23 |

FOREIGN PATENT DOCUMENTS

WO    WO 97/11734    4/1997

* cited by examiner

Primary Examiner—John G. Weiss
Assistant Examiner—Darwin P. Erezo
(74) Attorney, Agent, or Firm—Klehr, Harrison, Harvey, Branzburg & Ellers LLP; John F. Letchford

(57) ABSTRACT

Pneumatically operated gas demand equipment coupled in interruptible fluid communication between a recipient and a source of pressurized respiratory gas and adapted for controlling delivery of the pressurized gas to the recipient as the recipient inhales and exhales. The equipment includes a supply valve and a sensing valve cooperable to intermittently deliver pressurized gas to the recipient responsive to the recipient's inhalation and exhalation. A regulator mechanism is disposed between and in fluid communication with the pressurized gas source and the supply valve. The equipment additionally includes a control device for controlling flow of pressurized gas from the pressurized gas source to the supply valve and from the pressurized gas source to the regulator mechanism. The control device also controls the pressure of pressurized gas discharged by the regulator mechanism.

33 Claims, 8 Drawing Sheets

VARIABLE PRESSURE AND FLOW CONTROL FOR A PNEUMATICALLY-OPERATED GAS DEMAND APPARATUS

CROSS-REFERENCE TO RELATED APPLICATION

This application is related to U.S. patent application Ser. No. 09/405,420, filed on Sep. 22, 1999, entitled PNEUMATICALLY-OPERATED GAS DEMAND APPARATUS.

FIELD OF THE INVENTION

The present invention relates generally to respiratory equipment and, in particular, to a pneumatically-operated gas demand apparatus coupled in interruptible fluid communication between a recipient and at least one source of a pressurized gas and adapted for controlling delivery of the pressurized gas to the recipient as the recipient inhales and exhales.

BACKGROUND OF THE INVENTION

Many medical patients sufferings from any one of a variety of lung ailments are often prescribed supplemental oxygen therapy so that the patient could breathe oxygen-enriched air throughout the day and sometimes throughout the night. Earlier supplemental oxygen therapy employed a nasal cannula system operably connected between a tank of compressed oxygen and the patient's nose. Oxygen was continuously delivered to the patient throughout the patient's entire breathing cycle. This method of continuously delivering oxygen to the patient throughout the patient's breathing cycle was considered wasteful because much of the oxygen dissipated into the ambient air environment. Better method of delivering oxygen to the patient were later developed which included improved equipment that would only deliver oxygen to the patient during the inhalation phase of the patient's breathing cycle. Usually, this improved equipment employed a demand valve which opened to deliver supplemental oxygen to the patient only when the patient inhaled. Numerous types of demand valves are well known in the prior art.

One such demand valve is described in U.S. Pat. No. 5,360,000 to Carter. This demand valve is compact, simplified and totally pneumatic. The demand valve which is coupled between a source of pressurized gas such as oxygen and the patient includes a valve body having a gas flow passageway and pneumatically-coupled sensing and slave diaphragms. The slave diaphragm is interposed in the gas flow passageway and prevents gas from flowing during the exhalation phase of the patient's respiratory cycle. During inhalation, which is sensed by a sensing diaphragm, the slave diaphragm moves to open the gas flow passageway, thus permitting flow of gas to the patient. Although effective in delivering gas to a patient upon demand, this demand valve has an inherent problem. When the patient inhales to cause delivery of oxygen to patient, oxygen is also vented into the ambient air environment for as long as the slave diaphragm remains opened. This leads to wastage of oxygen which is the very problem that demand valves were designed to prevent.

Furthermore, this demand valve has an inherent deficiency of delivering gas to the patient in a continuous flow stream upon and during the inhalation phase. Unfortunately, the air remaining in the patient's respiratory passageway, i.e., the nasal cavity and the throat, is first taken into the lungs upon inhalation. The oxygen-enriched air then follows the remaining air and only approximately one-half of the oxygen-enriched air ever reaches the lungs. The remaining one-half of the oxygen-enriched air remains in the patient's respiratory passageway during the waning moments of inhalation and is the first to be exhaled therefrom during exhalation. It would be beneficial to the patient if this air remaining in the patient's respiratory passageway after exhalation could be purged or otherwise enriched with oxygen before it is inhaled. Such an approach is utilized in U.S. Pat. No. 4,686,974 to Sato et al.

U.S. Pat. No. 5,666,945 to Davenport, the disclosure of which is incorporated herein by reference, describes a pneumatically-operated gas demand apparatus which overcomes many of the deficiencies of prior devices. The Davenport apparatus includes cooperating supply and sensing valves in interruptible fluid communication between a recipient (or patient) and at least a first source of pressurized gas. The supply valve includes a supply valve housing with a first diaphragm member disposed therein. Similarly, the sensing valve includes a sensing valve housing and a second diaphragm member disposed therein. The Davenport apparatus is constructed such that, when the recipient inhales, the second diaphragm member assumes a flow-causing position and the first diaphragm member assumes a flow-supplying position whereby pressurized respiratory gas is delivered to the recipient. When the recipient exhales, the second diaphragm member assumes a flow-stopping position and the first diaphragm member assumes a flow-blocking position, thereby preventing delivery of the respiratory gas to the recipient.

The pneumatically-operated gas demand apparatus of Davenport also includes a bolus chamber structure, a supply orifice element and a pilot orifice element. The bolus chamber defining a bolus chamber therein is disposed between and in fluid communication with a regulator mechanism and a supply chamber region of the supply valve. The supply orifice element having a supply orifice formed therethrough is disposed between the regulator mechanism and the bolus chamber structure. The pilot orifice element having a pilot orifice extending therethrough is disposed between a source of pressurized respiratory gas and the supply valve.

The bolus chamber functions as a repository or accumulator for a volume of pressurized respiratory gas which is discharged during inhalation and recharged during exhalation by the recipient. The bolus chamber enables the apparatus to deliver a high-flow pulse of oxygen to the recipient upon commencement of the inhalation phase of the recipient's breathing cycle. The high-flow oxygen pulse advantageously enriches the air remaining in the recipient's airway upon inhalation and, simultaneously therewith, purges some of the air from the recipient's respiratory passageway. The Davenport device also delivers a continuous flow of oxygen immediately after delivery of the pulse of high-flow oxygen and for the remaining portion of inhalation whereby the recipient receives oxygen enriched respiratory gas throughout inspiration.

The intermittent gas delivery device of Davenport may also be used with a nebulizer. Pursuant to this modality, the high-flow pulse of oxygen delivered from the bolus chamber generates a fine mist of medicament-containing aerosol within the nebulizer which is inhaled by the recipient. The mist may thereafter be followed with a flow of pressurized respiratory gas for the remainder of inhalation.

In the Davenport device, the pulse volume is proportional to the supplied flow rate. Such a system works well in circumstances where the ratio of highest to lowest recipient demand flow rate is on the order of about three to about four to one. However, many patients have rather expansive demand flow ranges. Under these circumstances, the required flow ratio (which is an empirical ratio of the maximum to minimum demand flow rates) may become quite large. The flow requirements for some recipients, for example, may range from as low as about 0.5 lpm (liters per minute) for sedentary persons to as high as about 6 lpm for persons under physical stress. This maximum to minimum flow ratio would in turn require a pressure range of up to about 12:1 or more. Such a broad band of demand flow requirements impacts design and operation of the Davenport system in several significant ways.

First, the regulator mechanism must employ a high pressure regulator to reduce the high pressure supply gas to a workable level and a low pressure regulator to service the broad range of flow and pressure delivered by the system. The high pressure regulator must be capable of supplying respiratory gas at the higher pressure regions, and the supply (or pilot) valve must be reinforced to accommodate this higher pressure. In so doing, the dynamic performance of the supply valve ("on" and "off" timing, leakage flow, and the like) may be detrimentally affected. Second, an extremely small pilot orifice must be provided between the source of pressurized respiratory gas and a control region of the supply valve to ensure proper operation of the sensing valve. Third, the operating range of the low pressure regulator must be quite broad which may result in errors in the low pressure regulator and its adjustment mechanism that may become substantial at lower operational settings.

An advantage exists, therefore, for a pneumatically-operated gas demand apparatus capable of providing a high-flow pulse of pressurized respiratory gas upon commencement of the inhalation phase of a recipient's respiratory cycle and which reliably operates in flow ranges from as low as about 0.5 lpm to as high as 6 lpm or more. The apparatus also preferably should be usable with a nebulizer to generate and deliver a medicament-containing aerosol to a recipient on demand as the recipient inhales and exhales while minimizing wastage of oxygen. It would be advantageous if this pneumatically-operated gas demand apparatus can deliver a high-flow pulse of oxygen to the recipient/patient upon commencement of the inhalation phase of the patient's breathing cycle. Such a high-flow pulse of oxygen delivered upon commencement of the inhalation phase would enrich the air remaining in the patient's respiratory passageway upon inhalation and, simultaneously therewith, purge some of this air therefrom before being inhaled. It would also be advantageous if this pneumatically-operated gas demand apparatus can deliver a continuous flow of oxygen immediately after delivery of the pulse of high-flow oxygen and throughout the remaining portion of inhalation.

There is a further need in the industry to provide a selective controller for a pneumatically-operated gas demand apparatus that can simultaneously regulate pressure and flow of gas administered by the apparatus. The pressure and flow controller should be easy to use, reliable and capable of administering one or more high pressure boluses of pressurized gas at the onset of a recipient's inspiratory cycle and continuous flow for the remainder of the inspiratory cycle.

Published PCT Application No. WO 97/11734 describes an adjustable flow controller for a pneumatically-operated gas demand apparatus disposed between a conventional high pressure regulator and the supply chamber of the demand valve for selectively delivering gas at desired flow rates to the supply chamber. The flow controller is a rotor disk that is attached to a flow selector knob. The rotor disk is in fluid communication with the high pressure regulator and the supply chamber and includes a plurality of oxygen flow metering orifices of varying diameters. To select a desired flow rate, a user turns the selector knob until the appropriate orifice is aligned with the flow path leading to the supply chamber. If another flow rate is desired, the user turns the selector knob until another orifice of suitable diameter is brought into alignment with the path. A spring-biased ball and detent mechanism releasably retains the flow selector knob in each selected position.

The flow controller described in WO 97/11734 does not provide any additional pressure control of the gas beyond that provided by the high pressure regulator. That is, a recipient may receive gas at variable flow rates for each pressure established by the high pressure regulator. However, the flow controller cannot further modify the pressure set by the high pressure regulator. At certain flow rates or under certain therapeutic circumstances, it may be desirable to change the gas pressure to a level different from that established by the high pressure regulator without readjusting the setting of the high pressure regulator. The device described in WO 97/11734 does not provide this capability. Moreover, that device provides a constant volume bolus regardless of the flow setting. In addition, it takes longer for the bolus to recharge at lower flow rates. If a patient is taking short, quick breaths, the bolus does not have adequate time to recharge. Under those circumstances, the device would function in essence as if it were a constant flow device.

In addition, spring-biased ball and detent retention mechanisms such as that used to retain the rotor disk disclosed in WO 97/11734 are susceptible to wear. During use, the ball tends to become abraded by the spring as well as form a groove between the detents. The ball may thus become prematurely worn. Concomitantly, when sufficiently deep, the groove formed by the ball makes it difficult for a user to locate a desired detent and reduces a detent's ability to retain the ball.

A further advantage exists, therefore, for a pneumatically-operated gas demand apparatus having a pressure and flow controller which is reliable, easy to operate and capable of providing variable gas flow rates and pressure levels in pneumatically-operated gas demand apparatus having zero, one or more than one bolus chambers. Preferably, the pneumatically-operated gas demand apparatus also should be usable with a nebulizer to generate and deliver a medicament-containing aerosol to a recipient on demand.

SUMMARY OF THE INVENTION

An object of the present invention is to provide a pneumatically-operated gas demand apparatus for coupling in interruptible fluid communication between a recipient/patient and at least one source of pressurized respiratory gas such as oxygen. The apparatus should be operable to control delivery of oxygen to the recipient/patient as the recipient inhales and exhales while minimizing wastage of oxygen.

Another object of the present invention is to provide a pneumatically-operated gas demand apparatus which can deliver one or more high-pressure boluses of oxygen to the recipient/patient upon commencement of the inhalation phase of the recipient/patient's breathing cycle and a continuous flow of oxygen thereafter and throughout the remaining period of negative pressure defining the inhalation phase of the breathing cycle.

Another object of the present invention is to provide a pressure and flow controller which is reliable, easy to operate and capable of providing variable gas flow rates and pressure levels in pneumatically-operated gas demand apparatus having zero, one or more than one bolus chambers.

Yet another object of the present invention is to provide a pneumatically-operated gas demand apparatus which is simple in design and compact.

A still further object of the present invention is to provide a pneumatically-operated gas demand apparatus which can be fabricated from readily available components or can be integrated into a unitary construction.

Accordingly, a pneumatically-operated gas demand apparatus of the present invention is hereinafter described. The pneumatically-operated gas demand apparatus is coupled in interruptible fluid communication between a recipient (or patient) and a first source of a pressurized first gas and is adapted for controlling delivery of the first gas to the recipient as the recipient inhales and exhales. In its broadest form, the pneumatically-operated gas demand apparatus, like that disclosed in U.S. Pat. No. 5,666,945 to Davenport, includes a supply valve and a sensing valve. The supply valve includes a supply valve housing and a flexible first diaphragm member. The supply valve housing defines a first interior chamber formed therein. The first diaphragm member is disposed within the first interior chamber and is connected to the supply valve housing in a manner to divide the first interior chamber into a supply chamber region and a control chamber region. The supply chamber region is in interruptible fluid communication with and between the first source of the first gas and the recipient and the control chamber region is in continuous fluid communication with either the first source of pressurized gas or a second source of a pressurized second gas. The first diaphragm member is operative to hermetically seal the supply chamber region and the control chamber region from one another and is operative to move between a flow-blocking position and a flow-supplying position.

The sensing valve includes a sensing valve housing and a flexible second diaphragm member. The sensing valve housing defines a second interior chamber formed therein. The second diaphragm member is disposed within the second interior chamber and is connected to the sensing valve housing in a manner to divide the second interior chamber into a venting chamber region and a sensing chamber region. The venting chamber region is in interruptible fluid communication with and between the control chamber region of the first interior chamber of the supply valve and an ambient air environment and the sensing chamber region is in continuous fluid communication with the recipient. The second diaphragm member is operative to hermetically seal the venting chamber region and the sensing chamber region from one another and is responsive, when the recipient inhales and exhales, to move between a flow-stopping position and a flow-causing position. When the recipient inhales, the second diaphragm member is in the flow-causing position thereby causing either pressurized first gas or second gas to flow from the control chamber region, through the venting chamber region and into the ambient air environment which, in turn, causes the first diaphragm member to be in the flow-supplying position thereby delivering the first gas from the first source of pressurized first gas to the recipient. When the recipient exhales, the second diaphragm member is in the flow-stopping position thereby preventing gas flow from the control chamber region, through the venting chamber region and into the ambient air environment which, in turn, causes the first diaphragm member to be in the flow-blocking position thereby preventing delivery of the first gas to the recipient.

The pneumatically-operated gas demand apparatus also preferably includes a multiple bolus chamber structure, a plurality of supply orifice elements and a pilot orifice element. The multiple bolus chamber structure defining a plurality of bolus chambers therein is disposed between and in fluid communication with a pressure and flow controller and the supply chamber region of the supply valve.

Pursuant to a preferred embodiment, a dual bolus chamber construction operates to distribute the flow range of the apparatus between first and second bolus chambers. This division of flow requirements provides an arrangement whereby even broad recipient demand flow ranges, e.g., about 0.5 lpm to 6 lpm or more, may be easily accommodated without negatively impacting the performance of the supply valve, the sensing valve or the regulator mechanism.

In a preferred embodiment, the apparatus includes a pressure and flow control device disposed between and in fluid communication with a high pressure regulator, one or more bolus chambers (if present) and the supply chamber region of the supply valve. The pressure and flow control device can modify the pressure set by the high pressure regulator and provide various flow rates during operation of the apparatus. At certain selected flow rates, the pressure and flow control device can change the gas pressure to a level different from that established by the high pressure regulator without readjusting the setting of the high pressure regulator.

Preferably, when a plurality of pressurized gases are conveyed by the apparatus, the first gas and the second gas are oxygen and, therefore, the first gas and the second gas are the same. With the first and second gases being the same, the at least one gas source may comprise a first source and a second source of pressurized gas that could also, but not necessarily, be the same. The first gas and the second gas can be different from each other. If so, the first source and the second source must also be different from one another. The first gas and the second gas are selected from either different ones or the same one of a group of gases consisting of oxygen, nitrous oxide, air and other types of gases.

Other details, objects and advantages of the present invention will become apparent as the following description of the presently preferred embodiments and presently preferred methods of practicing the invention proceeds.

BRIEF DESCRIPTION OF THE DRAWINGS

The invention will become more readily apparent from the following description of preferred embodiments thereof shown, by way of example only, in the accompanying drawings, wherein.

DETAILED DESCRIPTION OF THE EXEMPLARY EMBODIMENTS

A pneumatically-operated gas demand apparatus is coupled in interruptible fluid communication between a recipient and a source of pressurized oxygen and is adapted for controlling delivery of oxygen to the recipient as the recipient inhales and exhales. Although the pneumatically-operated gas demand apparatus is specifically suited to provide oxygen to a recipient/patient, one of ordinary skill in the art would appreciate that the present invention can also be adapted and used to deliver other kinds of gases to recipients such as nitrous oxide. Further, since the pneumatically-operated gas demand apparatus can deliver and operate with either a single gas such as oxygen or two gases such as oxygen and inexpensive compressed air, other types of gases can also be employed without departing from the spirit and concepts of the present invention.

Figure 1:
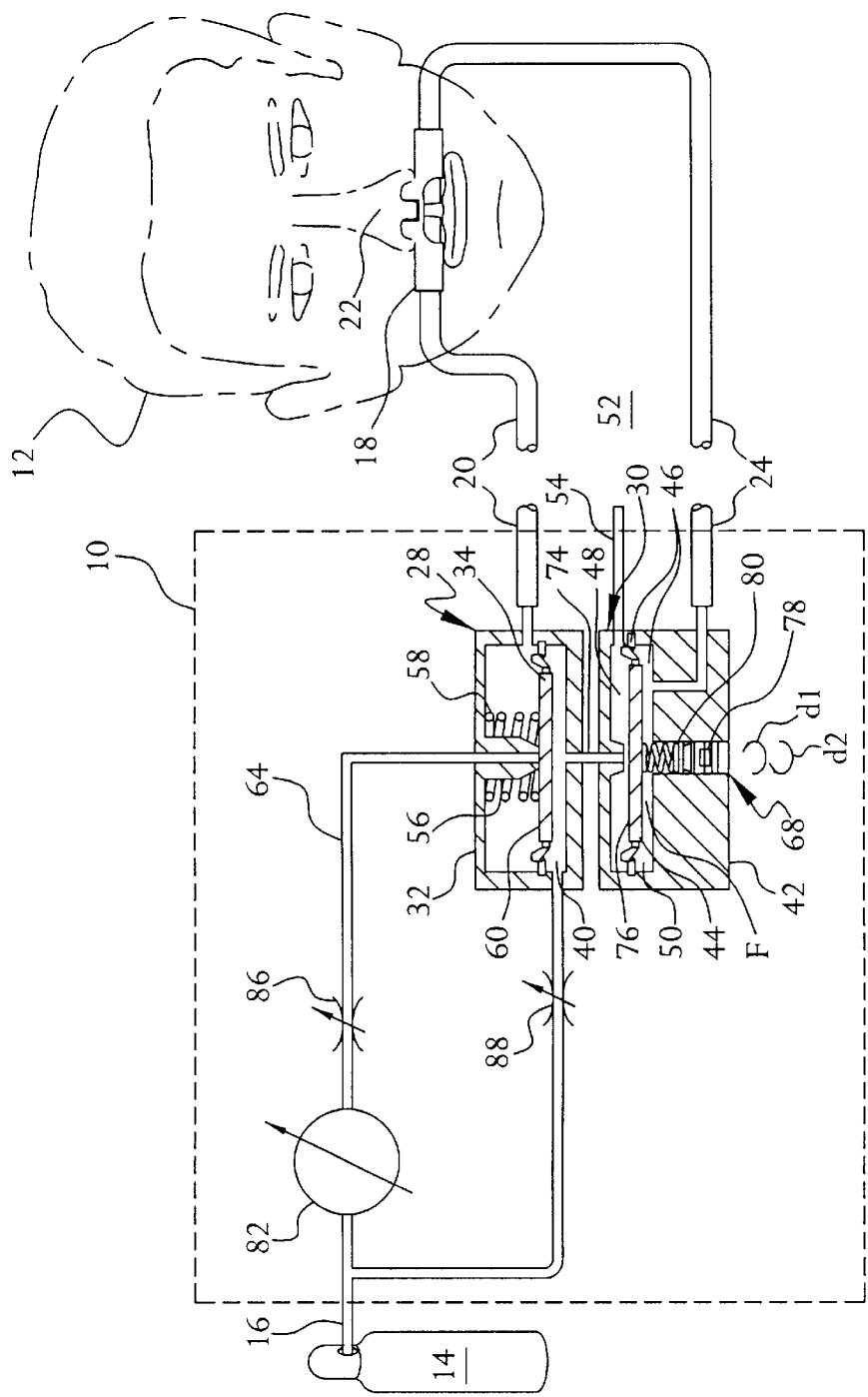
FIG. 1 is partially a schematic view and partially an elevational side view in cross-section of a typical pneumatically-operated gas demand apparatus coupled between and in fluid communication with a single source of pressurized gas and a recipient with a supply valve in a flow-blocking position and a sensing valve in a flow-stopping position as a result of the recipient exhaling.
Figure 2:
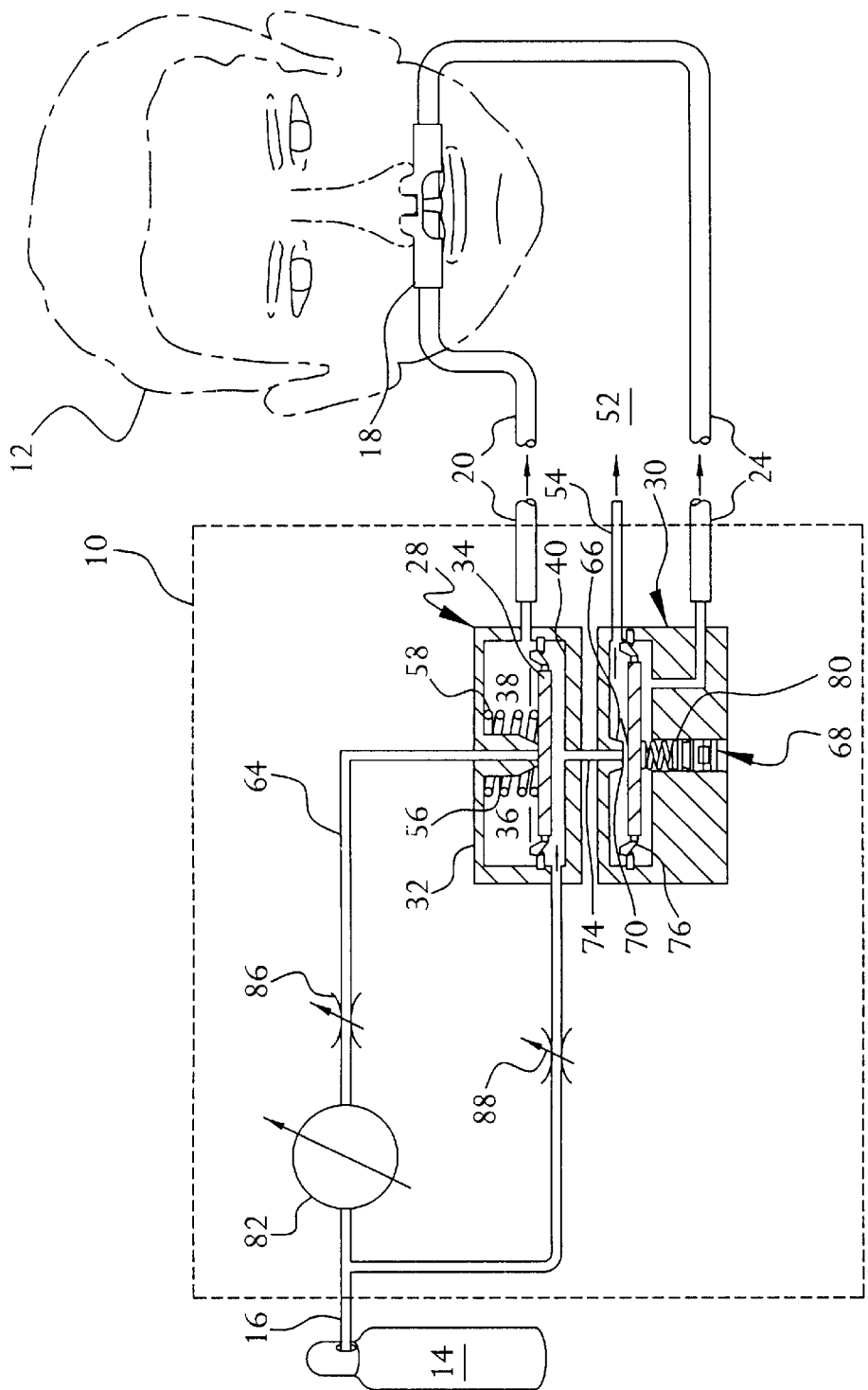
FIG. 2 is partially a schematic view and partially an elevational side view in cross-section of the pneumatically-operated gas demand apparatus of FIG. 1 shown coupled between and in fluid communication with the single source of pressurized gas and the recipient with the supply valve in a flow-supplying position and the sensing valve in a flow-causing position as a result of the recipient inhaling.

Referring to the drawings wherein like references indicate like elements throughout the several views, there is shown in FIGS. 1 and 2 a conventional pneumatically-operated gas demand apparatus 10 coupled in interruptible fluid communication between a recipient 12 and at least one source 14 of pressurized respiratory gas such as oxygen. Conventional tubing 16 interconnects pneumatically-operated gas demand apparatus 10 to source 14 and a partitioned, nasal cannula assembly 18 interconnects pneumatically-operated gas demand apparatus 10 and recipient 12. A dual-lumen, nasal cannula assembly (not shown) can also be employed and is well known in the art and no additional explanation thereof is deemed necessary to practice the present invention. A first lumen 20 of a dual-lumen, nasal cannula assembly 18 is connected between pneumatically-operated gas demand apparatus 10 and recipient 12 to conduct oxygen to a nose 22 of the recipient. A second lumen 24 is connected between pneumatically-operated gas demand apparatus 10 and cannula 18 to act as a conduit so that inhalation pressure and exhalation pressure to and from recipient 12 can be conveyed to and from pneumatically-operated gas demand apparatus 10. As a result, pneumatically-operated gas demand apparatus 10 is adapted for controlling delivery of gaseous oxygen to recipient 12 as the recipient inhales and exhales.

Again, with reference to FIGS. 1 and 2, pneumatically-operated gas demand apparatus 10 comprises a supply valve 28 and a sensing valve 30. Supply valve 28 includes a supply valve housing 32 and a flexible first diaphragm member 34. Supply valve housing 32 defines a first interior chamber 36 which is formed therein. Flexible first diaphragm member 34 is disposed within first interior chamber 36 and is connected to supply valve housing 32 in a manner to divide first interior chamber 36 into a supply chamber region 38 and a control chamber region 40. Supply chamber region 38 is in interruptible fluid communication with and between source 14 of the pressurized oxygen and recipient 12. Throughout the present description, the phrase, "interruptible fluid communication" is used and, by way of example only, "interruptible fluid communication" means that sometimes supply chamber region 38 is in fluid communication with source 14 while at other times supply chamber region 38 is not in fluid communication with source 14. Control chamber region 40 is in continuous fluid communication with source 14 of pressurized oxygen. First diaphragm member 34 is operative to hermetically seal supply chamber region 38 and control chamber region 40 from one another. Additionally, first diaphragm member 34 is operative to move between a flow-blocking position as shown in FIG. 1 and a flow-supplying position as shown in FIG. 2.

Sensing valve 30 includes a sensing valve housing 42 and a flexible second diaphragm member 44. Sensing valve housing 42 defines a second interior chamber 46 which is formed therein. Second diaphragm member 44 is disposed within second interior chamber 46 and is connected to sensing valve housing 42 in a manner to divide second interior chamber 46 into a venting chamber region 48 and a sensing chamber region 50. Venting chamber region 48 is in interruptible fluid communication with and between control chamber region 40 of first interior chamber 36 of supply valve 28 and an ambient air environment 52 through a bleed conduit 54. Sensing chamber region 50 is in continuous fluid communication with recipient 12.

Second diaphragm member 44 is operative to hermetically seal venting chamber region 48 and sensing chamber region 50 from one another. Further, second diaphragm member 44 is responsive when recipient 12 inhales and exhales by moving between a flow-stopping position as shown in FIG. 1 and a flow-causing position as shown by FIG. 2. As best shown in FIG. 2, when recipient 12 inhales, second diaphragm member 44 is in the flow-causing position thereby causing oxygen (represented by the single solid line arrows) to flow from control chamber region 40, through venting chamber region 48 and into ambient air environment 52. In turn, second diaphragm member 44 being in the flow-causing position causes first diaphragm member 34 to be in the flow-supplying position thereby delivering oxygen from source 14 of pressurized oxygen to recipient 12. As shown in FIG. 1, when recipient 12 exhales, second diaphragm member 44 is in the flow-stopping position thereby preventing oxygen to flow from control chamber region 40, through venting chamber region 48 and into ambient air environment 52, which, in turn, causes first diaphragm member 34 to be in the flow-blocking position thereby preventing delivery of oxygen to recipient 12.

Supply valve 28 includes a supply tube stem 56 and a supply valve spring 58. Supply tube stem 56 is disposed within supply chamber region 38 of supply valve 28 and has a supply seat 60 defining a supply opening of a tube stem conduit 64. Tube stem conduit 64 provides fluid communication into supply chamber region 38. Supply seat 60 is sized and adapted to removably contact a blocking side of first diaphragm member 34 in a fluid-tight relation when supply valve 28 is in the flow-blocking position as shown in FIG. 1. Also, as shown in FIG. 2, the first diaphragm member 34 is in a spaced-apart, facially-opposing relationship with the supply opening of the tube stem conduit 64 when supply valve 28 is in the flow-supplying position. Supply valve spring 58 is disposed within supply chamber region 38 and surrounding supply tube stem 56. Supply valve spring 58 is operative to yieldably urge first diaphragm member 34 into the flow-supplying position.

Sensing valve 30 includes a sensing valve seat member 66 and a sensing valve adjustment assembly 68. Sensing valve seat member 66 is disposed in and extends into venting chamber region 48. Sensing valve seat member 66 has a sensing valve seat 70 which defines a flow opening into a supply valve conduit 74. Supply valve conduit 74 provides fluid communication into venting chamber region 48 of sensing valve 30. Sensing valve seat 70 is sized and adapted to removably contact second diaphragm member 44 in a fluid-tight relation when sensing valve 30 is in the flow-stopping position as shown in FIG. 1. The flow opening of supply valve conduit 74 is in a spaced-apart, facially-opposing relationship from second diaphragm member 44 when sensing valve 30 is in the flow-causing position as shown in FIG. 2.

Sensing valve adjustment assembly 68 includes a set screw 78 and a sensing valve spring 80. Set screw 78, threadably mounted into sensing valve housing 42, extends into sensing chamber region 50 and is accessible exteriorly of sensing valve housing 42. Sensing valve spring 80 is disposed within sensing chamber region 50 and in contact with and between set screw 78 and second diaphragm member 44. Sensing valve spring 80 imparts a yieldable tension force "F", shown in FIG. 1, to second diaphragm member 44 against sensing valve seat 70 to resiliently bias second diaphragm member 44 into the flow-stopping position. As commonly known in the art, turning set screw 78 in a first direction "$d_1$" increases tension force "F" and turning set screw 78 in a second direction "$d_2$" opposite the first direction "$d_1$" decreases the tension force "F".

Pneumatically-operated gas demand apparatus 10 includes a conventional regulator mechanism 82 (drawn symbolically), a supply orifice element 86 (drawn symbolically) and a pilot orifice element 88 (drawn symbolically). Regulator mechanism 82 would be disposed between and in interruptible fluid communication with source 14 of pressurized oxygen and supply chamber region 38 of supply valve 28. Pilot orifice element 88 is disposed between source 14 of the pressurized oxygen and control chamber region 40 of supply valve 28. By way of example and not limitation, pilot orifice element 88 and supply orifice element 86, as reflected by the symbolic drawings, may be of an adjustable, variable orifice type which are commonly known in the art.

Figure 3:
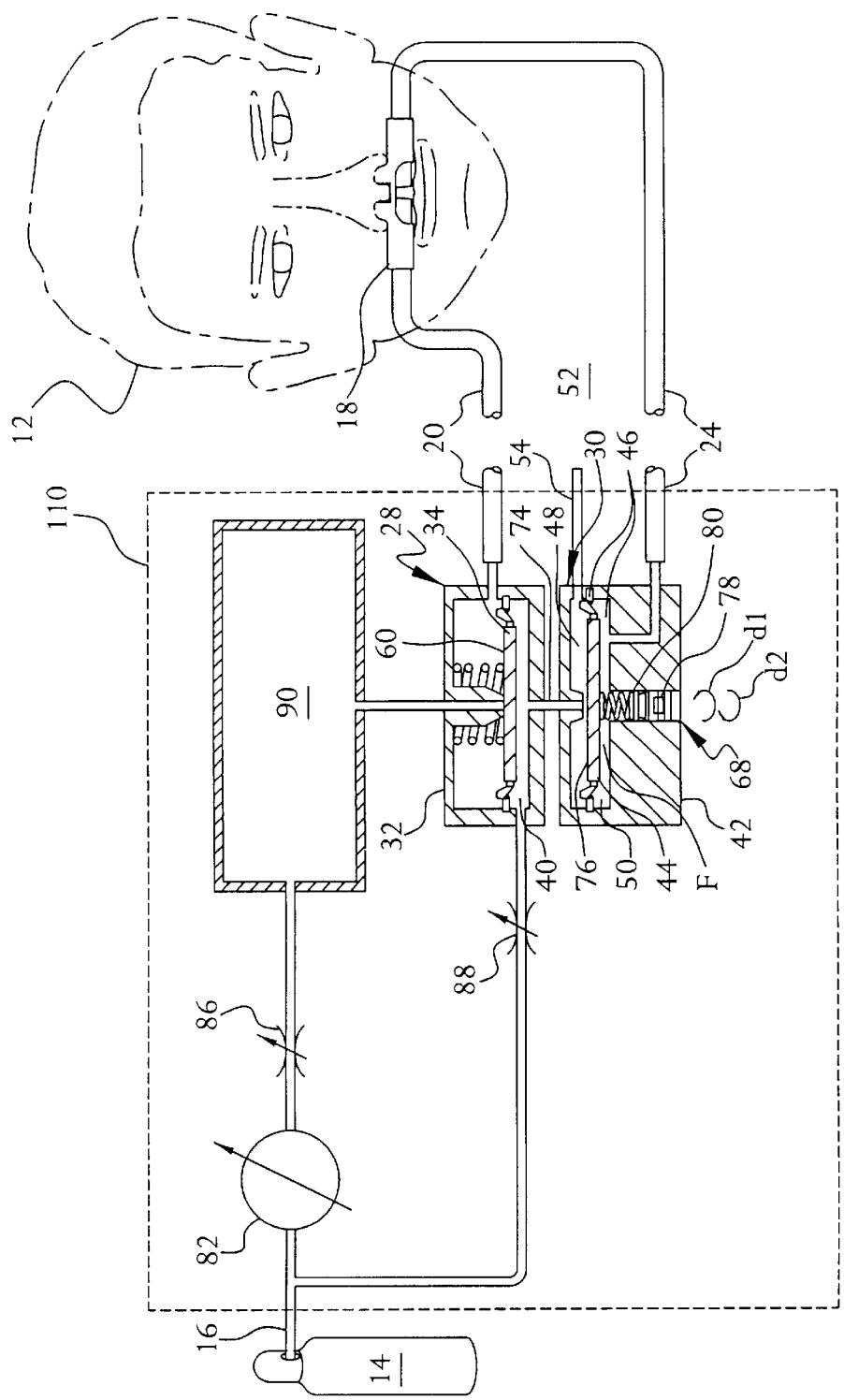
FIG. 3 is partially a schematic view and partially an elevational side view in cross-section of another known pneumatically-operated gas demand apparatus coupled between and in fluid communication with a single source of pressurized gas and a recipient with a supply valve in a flow-blocking position and a sensing valve in a flow-stopping position as a result of the recipient exhaling.

Referring to FIG. 3, there is shown a pneumatically-operated gas demand apparatus 110 constructed generally in accordance with that disclosed in U.S. Pat. No. 5,666,945 to Davenport. Unlike apparatus 10 discussed above, apparatus 110 includes a bolus chamber structure 84 defining an internal chamber 90 therein. The bolus chamber structure 84 is disposed between and in fluid communication with regulator mechanism 82 and supply chamber region 38 of supply valve 28. Supply orifice element 86 is disposed between regulator mechanism 82 and the bolus chamber structure 90. Pilot orifice element 88 is disposed between source 14 of the pressurized oxygen and control chamber region 40 of supply valve 28. The purpose of the bolus chamber structure 84 is to enable apparatus 110 to deliver a high-flow burst of oxygen or other pressurized respiratory gas upon initiation of inhalation in order to enrich the air in the patient's airway with the delivered respiratory gas. In all other respects, apparatus 110 is constructed and functions substantially similarly to apparatus 10.

Figure 4:
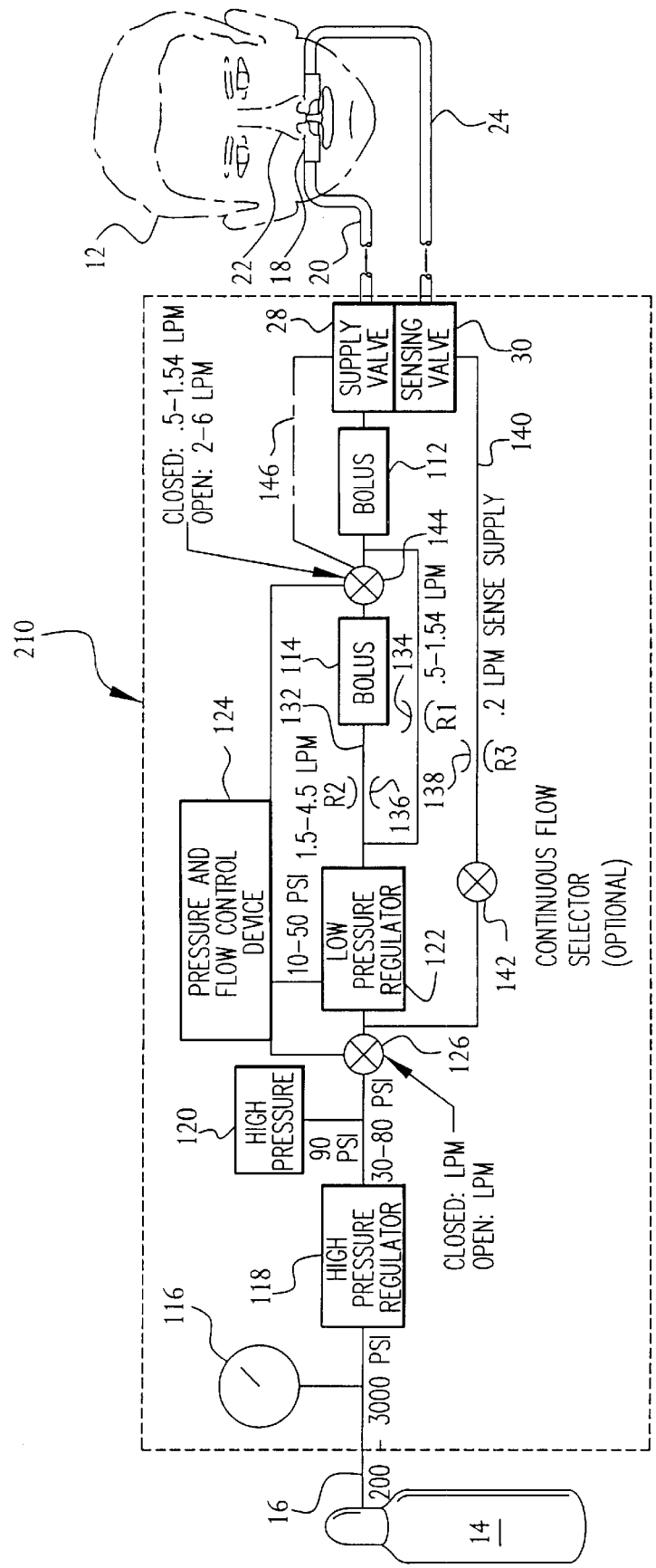
FIG. 4 is a schematic view of a pneumatically-operated gas demand apparatus according to the present invention coupled between and in fluid communication with a single source of pressurized gas and a recipient.
Figure 5:
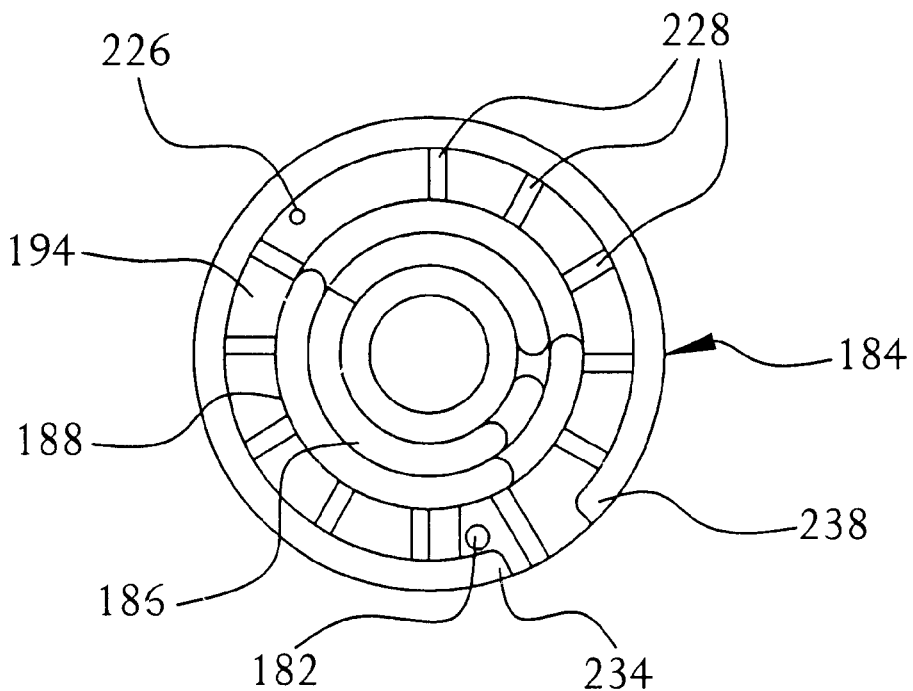
FIG. 5 is a top plan view of a cam plate of the supply valve of a pneumatically-operated gas demand apparatus according to the present invention.
Figure 6:
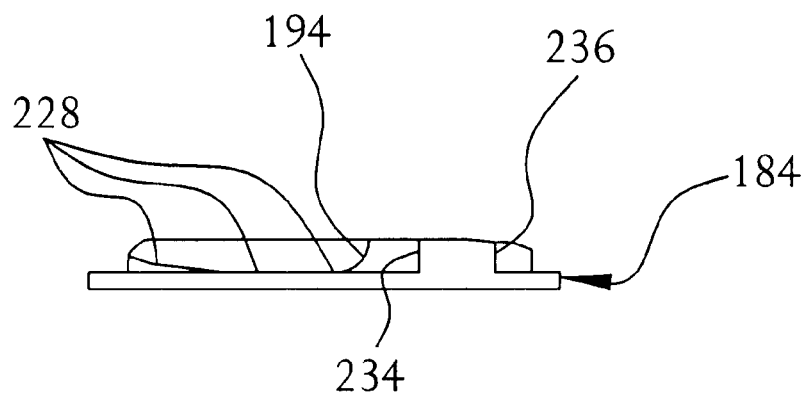
FIG. 6 is a side view of the cam plate of FIG. 5.

Referring to FIG. 4, there is shown a schematic representation a of pneumatically-operated gas demand apparatus constructed in accordance with a preferred embodiment of the present invention and identified generally by reference numeral 210. Pneumatically-operated gas demand apparatus 210 comprises a supply valve 28 and a sensing valve 30 constructed similarly to the supply and sensing valves of the pneumatically-operated gas demand apparatus 10 and 110 discussed above. In addition, apparatus 210 preferably includes first and second bolus chamber structures respectively defining first and second bolus chambers 112 and 114 therein.

When the source 14 of respiratory gas is a pressurized cylinder of oxygen, nitrous oxide or the like, the respiratory gas is typically discharged at a pressure of between about 200–3000 psi, which pressure may be detected on a conventional pressure gauge 116 either connected to tubing 16 or, as illustrated, integrated into apparatus 210. As set forth in greater detail hereinafter, apparatus 210 further includes, depending on its intended use or application, a regulator mechanism comprising one or more pressure regulators for controlling the pressure and flow rate of respiratory gas delivered by the apparatus to recipient 12. When configured to administer respiratory gas from a highly pressurized source 14, the regulator mechanism of apparatus 210 preferably comprises an internal (as illustrated) or external high pressure regulator 118 for reducing the gas pressure from source 14 to about 50–80 psi. The system further preferably includes a suitable relief valve 120 such as a check valve, poppet valve or the like, operable to release excess gas pressure about above 90 psi in the event of failure of the high pressure regulator 118, which pressure might otherwise cause malfunction and/or damage to apparatus 210.

According a presently preferred embodiment, the regulator mechanism of apparatus 210 also includes a low pressure regulator 122. Low pressure regulator 122 preferably functions in a range of about 10–50 psi and is operable to be used in conjunction with high pressure regulator 118, as shown, when the source 14 of respiratory gas is highly pressurized, or by itself when the source 14 is liquid oxygen or an air compressor. For example, when apparatus 210 is used to power a nebulizer on demand, i.e., only during the early stages of inhalation, source 14 would likely be a comparatively low pressure air compressor.

Apparatus 210 further preferably includes a pressure and flow control device 124. According to a presently preferred construction, pressure and flow control device 124 comprises cooperating means including a rotatable member, described in more detail in reference to FIGS. 5–8, for controlling gas flow to the low pressure regulator 122 and supply valve 28, gas pressure discharged by the low pressure regulator 122 and gas flow from one bolus chamber to another bolus chamber or to supply valve 28. The pressure and flow control device 124 preferably includes first flow control means 126 that is disposable into a CLOSED position whereby gas flow to the low pressure regulator 122 and the recipient 12 is shut off (FIG. 8). When in a range of OPEN positions, the first flow control means 126 is operable to deliver pressurized gas flow in a desired range, for example, about 0.5–6 lpm, to the low pressure regulator 122.

From the low pressure regulator 122 gas flow is communicated through a first passageway 128 to first bolus chamber 112 and through a second passageway 132 to second bolus chamber 114. Bolus chambers 112 and 114 distribute the recipient demand flow requirements of apparatus 210 in such a way that wide ranges of demand flow may be accommodated by the apparatus without detrimentally affecting its performance. Passageways 128, 132 split the gas flow to the bolus chambers 112, 114 such that neither bolus chamber operates under a pressure range that could deleteriously impact operation of the apparatus. More specifically, first passageway 128 is provided with a fixed or, more preferably, an adjustable, variable orifice type supply orifice element 134 of conventional construction which is operable to deliver gas flow at a rate of about 0.5 to about 1.5 lpm to bolus chamber 112. Accordingly, the pressure range of bolus chamber 112 is about 3:1 (i.e., which causes a flow ratio of approximately 1.5 lpm/ 0.5 lpm). Similarly, passageway 132 is provided with a conventional fixed or, more preferably, an adjustable, variable orifice type supply orifice element 136 operable to deliver gas flow at a rate of about 1.5 to about 4.5 lpm to bolus chamber 114. Hence, the pressure range of bolus chamber 114 is also about 3:1 (i.e., which causes a flow ratio of approximately 4.5 lpm/ 1.5 lpm).

Apparatus 210 also desirably includes a conventional fixed or, more preferably, an adjustable, variable orifice type sensing or pilot orifice element 138. The pilot orifice element 138 is disposed in a passageway 140 between the first flow control means 126 and the control chamber region 40 of supply valve 28. Since the control chamber region 40 of supply valve 28 is in fluid communication with the sensing valve 30 during inhalation, FIG. 4 depicts an inspiration phase whereby the pilot orifice element 138 communicates with sensing valve 30. When the first flow control means 126 of pressure and flow control device 124 is in the OPEN position, pilot orifice element 138 may deliver a flow of up to about 0.2 lpm of pressurized respiratory gas to the supply valve 28, which flow is communicated to the sensing valve 30 during inspiration. Passageway 140 may also include a continuous flow selector 142 if the pilot orifice element 138 is of the fixed-flow variety.

In addition to the first flow control means 126, pressure and flow control device 124 also preferably comprises a second flow control means 144 that is disposable into a CLOSED position (FIG. 8) whereby gas flow from bolus chamber 114 is shut off and the only flow delivered by apparatus 210 to supply valve 28 is that conveyed by passageway 128 to bolus chamber 112. Thus, when the recipient 12 inhales, he or she receives a comparatively low-level bolus of respiratory gas from bolus chamber 112 at the onset of inhalation followed thereafter by a continuous flow of between 0.5–1.5 lpm flow of respiratory gas for the remainder of the inspiratory phase. Such low bolus discharge and flow rates may be desirable, for example, to conserve oxygen during use by sedentary persons.

When the second flow control means 144 is in the OPEN position (FIG. 7) and recipient 12 inhales, at the onset of inhalation the recipient receives through supply valve 28 the combined boluses from bolus chambers 112 and 114. Thereafter the recipient receives the combined flows conveyed by passageways 128 and 132 (i.e., about 2–6 lpm) for the remainder of the inhalation phase. The bolus chambers 112, 114 may be connected in series relationship (FIGS. 7 and 8) or parallel relationship. That is, apparatus 210 may be configured such that bolus chamber 114 discharges either into bolus chamber 112 or directly into supply valve 28.

Distributing a typical demand flow range of about 0.5–6 lpm among several bolus chambers produces several advantages over systems involving a single bolus chamber. First, the pressure ranges may be significantly reduced, e.g., from as much as about 12:1 or more for a single bolus chamber design to about 3:1 for each chamber of a double bolus chamber design. The significantly reduced pressure ranges for each of the multiple bolus chambers effectively combine to eliminate dynamic performance problems in both the supply and sensing valves. Additionally, the low pressure regulator 122 may be selected to have a relatively restrictive operating range (e.g., about 10–40 psi) whereby errors in the operation of the low pressure regulator are avoided, even at low-flow system settings.

Figure 7:
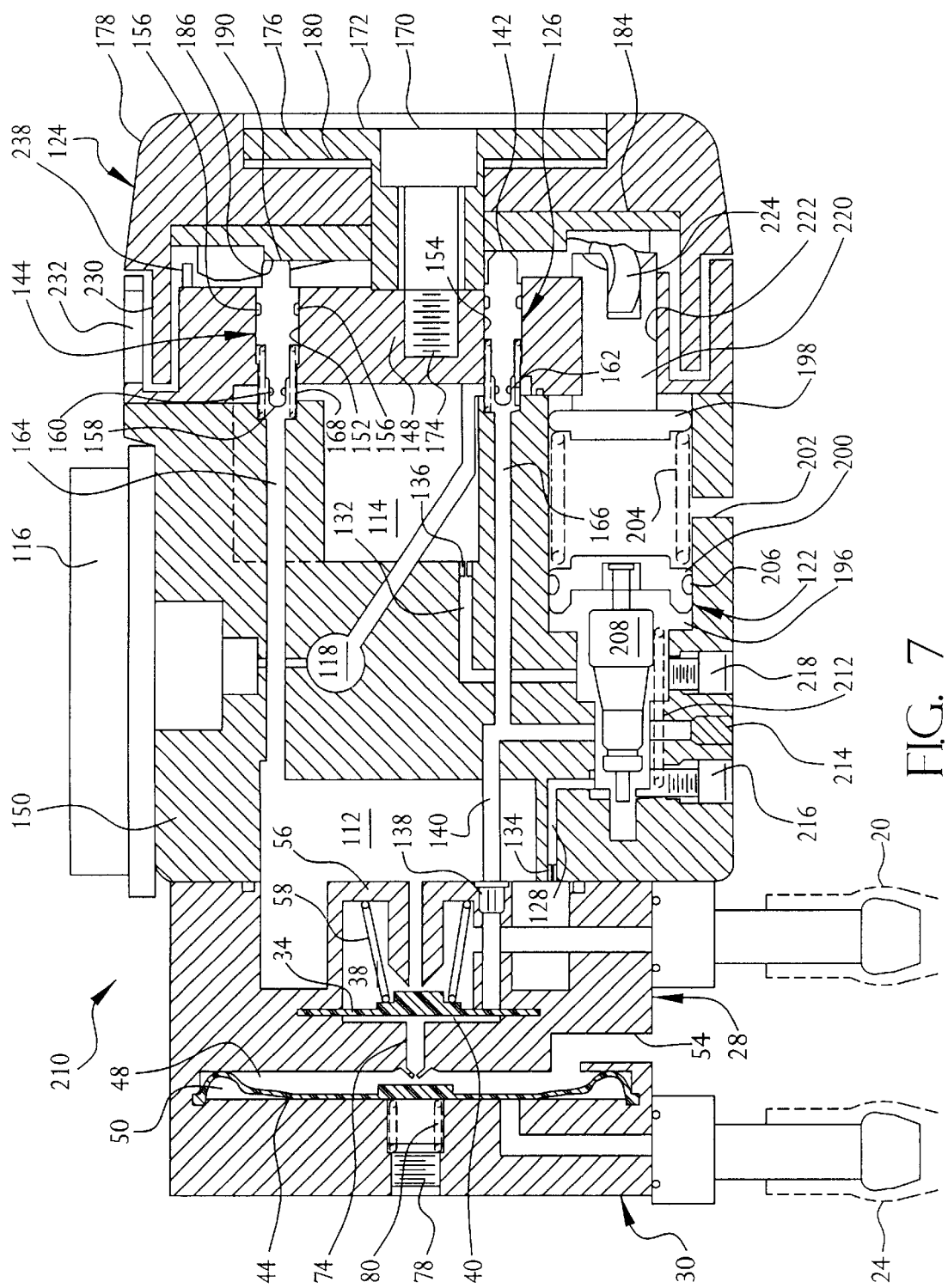
FIG. 7 is partially a schematic view and partially an elevational side view in cross-section of an exemplary embodiment of the pneumatically-operated gas demand apparatus of the present invention integrating the supply valve, the sensing valve and a regulator mechanism into a unitary construction with several pressure and flow control valves of a pressure and flow controller shown in open condition.
Figure 8:
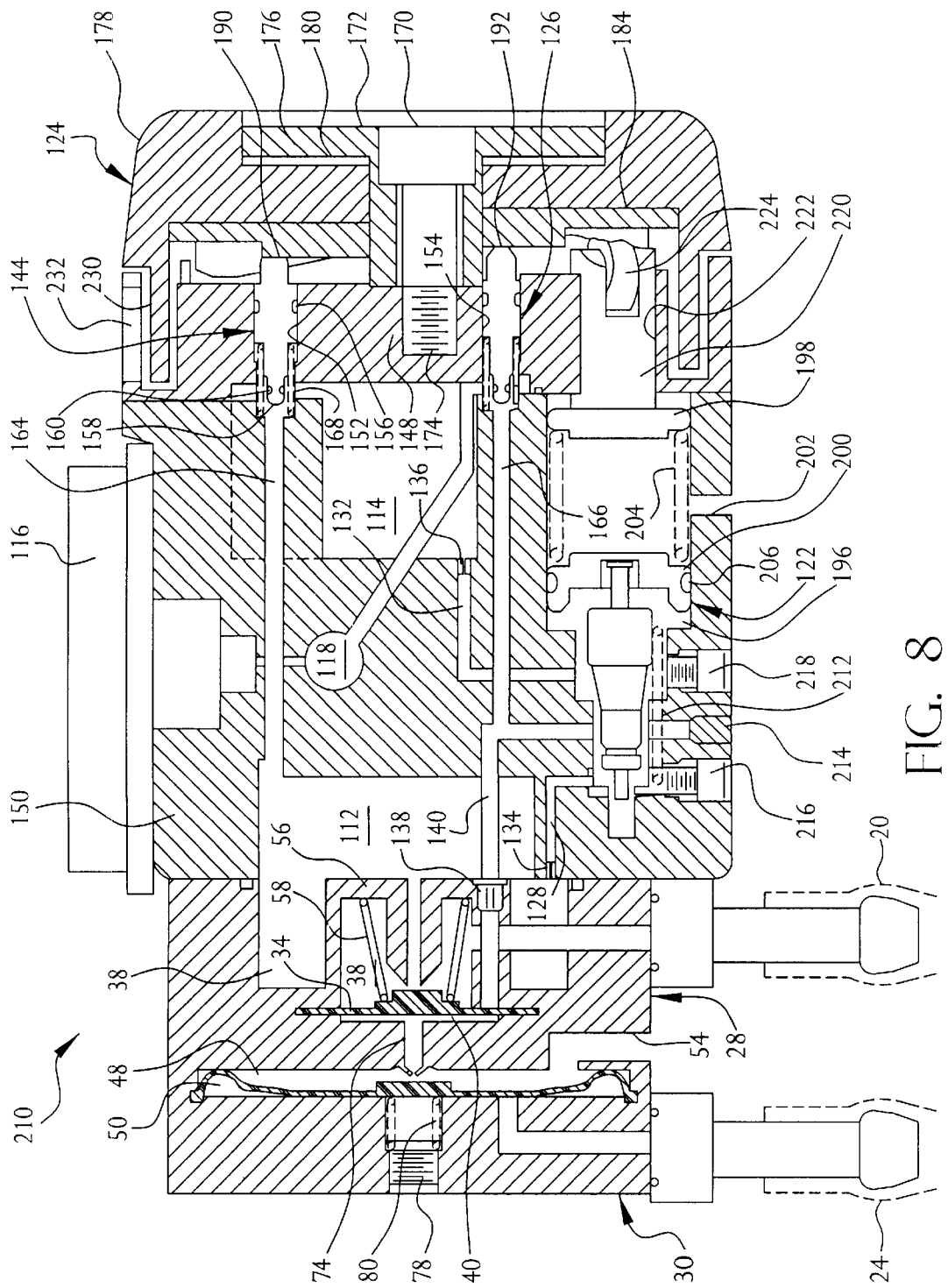
FIG. 8 is partially a schematic view and partially an elevational side view in cross-section of an exemplary embodiment of the pneumatically-operated gas demand apparatus of FIG. 7 with several pressure and flow control valves of a pressure and flow controller shown in closed condition.

FIGS. 5–8 provide greater resolution of the presently preferred construction of apparatus 210 in general and pressure and flow control device 124 in particular. As seen in FIGS. 7 and 8, pressure and flow control device 124 preferably comprises an interface plate 148 that may be affixed to a central body member 150 of apparatus 210 by suitable fastening means such as a plurality of screws or the like (not illustrated). Interface plate 148 includes first and second bores 152 and 154 for slidably receiving first and second flow control means 126, 144, respectively. Each of first and second flow control means 126, 144 is sealed with respect to bores 152, 154 by suitable annular sealing means 156 such as an O-ring or the like received in a groove provided in the flow control means. Each of the flow control means 126, 144 further includes a reduced diameter portion 158 which carries an annular sealing means 160 such as an O-ring 162. The reduced diameter portions 158 of the first and second flow control means 126, 144 are respectively adapted to be slidingly and sealingly received in passageways 164 and 166 provided in central body member 150. Each flow control means 126, 144 is biased away from the central body member 150 by a compression spring 168 captured between opposed unnumbered shoulders provided in the central body member 150 and the respective flow control means.

A bolt or screw 170, the shaft of which passes through a bushing 172, threadedly connects to interface plate 148 at 174. Bushing 172 desirably has an annular radially projecting flange 176 and rotatably supports a manually turnable knob 178. Desirably, thrust bearing means 180 in the form of a layer of polyethylene, polypropylene, polytetrafluoroethylene or other suitable rugged, low-friction material is disposed between flange 176 and an outer face of knob 178 to enable smooth rotation of the knob relative to the busing 172.

The inner face of knob 178 is preferably fitted with a dowel pin (not shown) or similar retaining means for engaging a bore 182 provided in a cam plate 184 (FIG. 5) whereby the cam plate is keyed to rotate with the knob upon turning of the knob by a user. Cam plate 184 is desirably formed with a plurality of concentrically arranged cam surfaces which perform discrete yet cooperating functions in the pressure and flow control device 124. The cam surfaces preferably comprise at least a first or main cam surface 186 for controlling operation of first flow control means 126. Flow control means 126 regulates gas flow to the supply valve 28. According to a presently preferred embodiment wherein apparatus includes low pressure regulator 122, first flow control means also controls flow to the low pressure regulator. Also according to the presently preferred construction, apparatus 210 further includes first and second bolus chambers 112, 114 connected in series by passageway 164. According to this construction, operation of the second flow control means 144 is controlled by a second cam surface 188 formed in cam plate 184. It will be understood, however, that the second bolus chamber may be connected to the supply valve 28 in parallel with the first bolus chamber 112 via an unillustrated passageway (see dot-dash line 146 in FIG. 4). In such case, the second flow control means 144 would still be required and would remain under the influence of second cam surface 188.

The tip or face 190 of first flow control means 126 (FIGS. 7 and 8) is biased into contact with first cam surface 186 by spring 168. Likewise, the tip or face 192 of second flow control means 144 is similarly biased into contact with second cam surface 188.

In the preferred construction, apparatus 210 includes low pressure regulator 122. Pursuant to that construction, cam plate 184 preferably comprises a third or pressure control cam surface 194 for controlling the pressure of gas discharged by the low pressure regulator 122 to the supply valve 28 and the first and/or second bolus chambers 112, 114 (if present).

Low pressure regulator 122 is preferably constructed as a floating assembly that is slidably received in a chamber 196 provided in the central body member 150 of apparatus 210. More specifically, low pressure regulator 122 comprises first and second disk means 198 and 200 between which is disposed an atmosphere vent port 202 in central body member 150. First and second disk means 198, 200 are biased apart from one another by a compression spring 204. The periphery of second disk means 200 is sealed with respect to the inner wall of chamber 196 by sealing means 206 such as an O-ring or the like. Low pressure regulator 122 further comprises a suitably configured valve means 208 such as a Shraedar or similar valve, one end of which is received in a face of second disk means 200 opposite spring 204. Through valve means 208, low pressure regulator 122 controls the pressure of gas discharged into passageways 128 and 132, which passageways are interconnected with chamber 196 via a passageway (indicated by dashed line 212). Passageways 140 and 166 are also in fluid communication with chamber 196. Passageways 140, 166 and chamber 196 are sealed from the ambient atmosphere via plug means 214. Flow control through passageways 128 and 132 is preferably effectuated by needle or similar valve means 216 and 218, respectively, threaded into the central body member 150 in operative alignment with passageways 128, 132.

Pressure and flow control device 124 further preferably comprises a cam follower support 220 slidably received in a through-bore 222 provided in interface plate 148. At one end, cam follower support 220 abuttingly contacts the face of first disk means 198 opposite spring 204 and, at an opposite end thereof, preferably rotatably supports a cam follower 224 such as a ball or, as illustrated, a roller. With low pressure regulator 122 so constructed, compression spring 204 biases cam follower 224 into contact with third cam surface 194 of cam plate 184. An advantage of low pressure regulator 122, especially when used in combination with pressure and flow control device 124, is that it enables additional gas pressure regulation beyond the pressure setting established by the high pressure regulator 118. This functionality may be desirable at certain gas flow rates or under certain therapeutic circumstances and allows gas pressure regulation without readjusting the setting of the high pressure regulator. Moreover, the cam and cam follower construction shown in FIGS. 7 and 8 is a low-wear assembly which promotes smooth, reliable and long-lasting performance of pressure and flow control device 124.

Cam follower support 220 desirably threadably receives an unillustrated adjustment member such as a screw or the like that may be accessed through an aperture 226 in cam plate 184 (FIG. 5) to enable fine tuning of the degree of compression of spring 204 and, thus, pressure regulation provided by the low pressure regulator 122.

A representative, although not limitative, example of combinations of flow rates and pressures attainable by apparatus 210 equipped with low pressure regulator 122 and pressure and flow control device 124 is shown in TABLE 1.

TABLE 1

| KNOB POSITION | TOTAL FLOW | LOW PRESSURE REGULATOR DISCHARGE PRESSURE | FIRST FLOW CONTROL MEANS POSITION | SECOND FLOW CONTROL MEANS POSITION |
|---|---|---|---|---|
| 1 | 0 | 0 | OFF | OFF |
| 2 | 0.5 | 10 | ON | OFF |
| 3 | 1.0 | 20 | ON | OFF |
| 4 | 1.5 | 30 | ON | OFF |
| 5 | 2.0 | 10 | ON | ON |
| 6 | 2.5 | 12.5 | ON | ON |
| 7 | 3.0 | 15 | ON | ON |
| 8 | 3.5 | 17.5 | ON | ON |
| 9 | 4.0 | 20 | ON | ON |
| 10 | 4.5 | 23.3 | ON | ON |
| 11 | 5.0 | 26.6 | ON | ON |
| 12 | 6.0 | 30 | ON | ON |

Third cam surface 194 is preferably provided with a plurality of radically disposed recessed landings 228 (FIGS. 5 and 6) for releasably retaining cam follower 224. Landings 228 enable the user to selectively dispose pressure and flow control device 124 at desired pressure and flow settings. Preferably, such settings are marked by suitable indicia provided on an annular surface 230 of knob 178 that is visible through an opening 232 provided in an outer peripheral wall of interface plate 148. Rotation of knob 178 is preferably limited to less than 360° by virtue of first and second stops 234, 236 (FIGS. 5 and 6) formed in cam plate 184 which are adapted to contact a dowel pin or similar lug means 238 (FIG. 7) outwardly projecting from interface plate 148.

Figure 9:
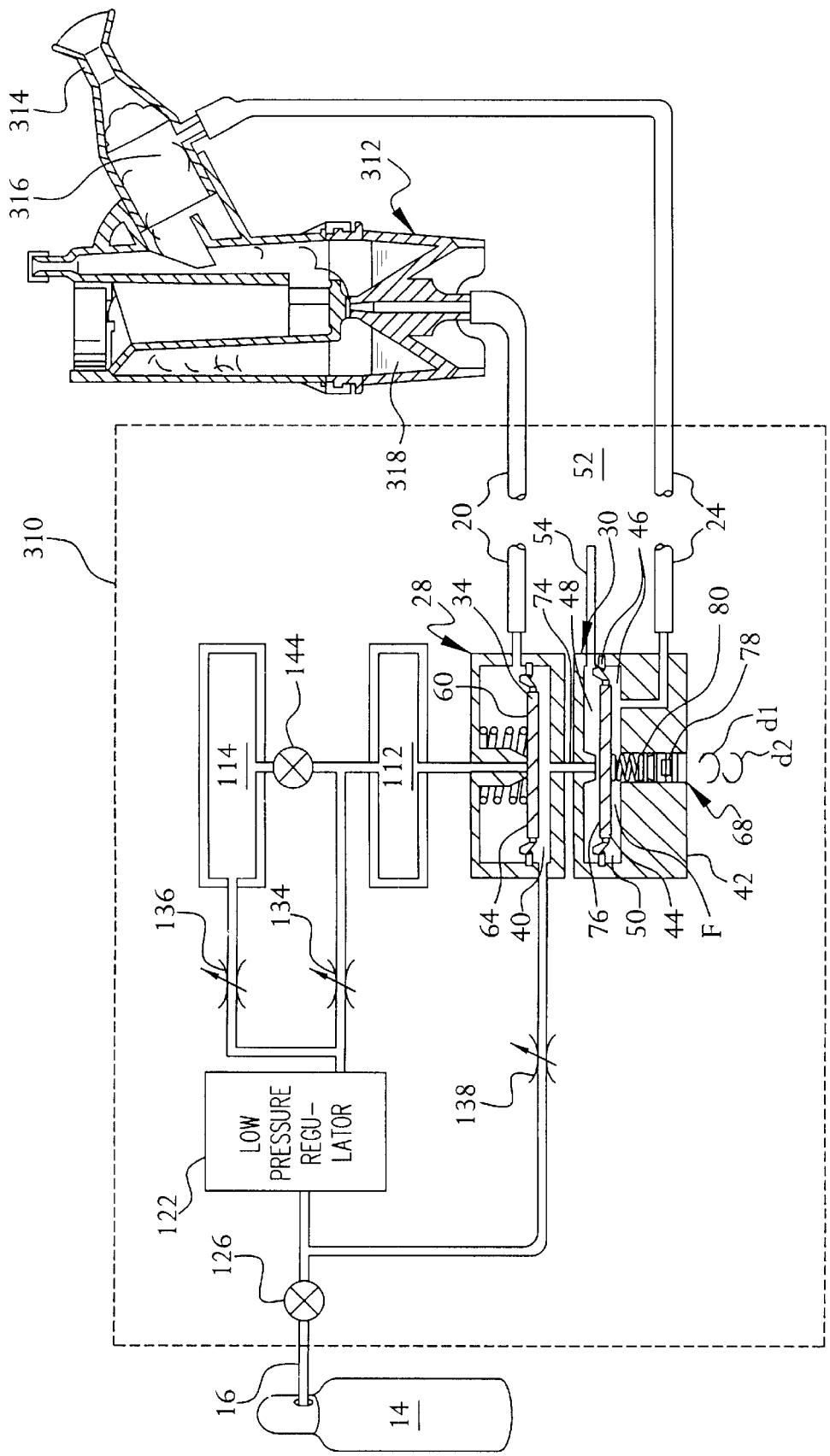
FIG. 9 is partially a schematic view and partially an elevational side view in cross-section of a further embodiment of the present invention constructed as an intermittent gas delivery device used in communication with a conventional nebulizer.

As shown in FIG. 9, it is also contemplated that many components of pneumatically-operated gas demand apparatus of FIGS. 7 and 8 can be combined with other components to construct an intermittent gas delivery device 310. Such intermittent gas delivery device could be utilized, for example, with a nebulizer such as the one described in U.S. Pat. No. 5,584,285 to Chua, et al. Other nebulizers are commonly known in the art and can be employed if equipped with an inhalation sensing structure or supplemental sensing apparatus. The elements of device 310 that bear like or similar reference numerals to elements of other apparatus discussed hereinabove may be considered structurally and functionally equivalent to their counterparts in those figures and thus will not be described in detail in connection with FIG. 9 except where necessary to provide a proper understanding of the invention.

Intermittent gas delivery device 310 is preferably connected in fluid communication between source 14 of pressurized gas, such as low pressure air or oxygen, and a nebulizer 312 via first and second lumens 20, 24 in the manner illustrated. A high pressure regulator is not required for proper functioning of apparatus 310 and would therefore normally be omitted therefrom. Inhalation by the user on the mouthpiece 314 of nebulizer 312 causes supply valve 28 and sensing valve 30 to provide gas flow to the nebulizer 312. During inhalation, nebulizer 312 generates a fine-mist plume 316 of a medicament-containing aerosol by virtue of pressurized gas entering the nebulizer through first lumen 20 and aerosolizing liquid medicament 318 contained in the nebulizer. Exhalation by the user causes supply valve 28 and sensing valve 30 to cease gas flow to nebulizer 312, thereby halting aerosolization of medicament 318. So constructed, intermittent gas delivery device 310 makes far more efficient use of medicament 318 than presently known continuous flow nebulizer apparatus that continuously aerosolize the medicament and wastefully vent the aerosolized medicament during the user's exhalation cycle.

Although the invention has been described in detail for the purpose of illustration, it is to be understood that such detail is solely for the purpose and that variations can be made therein by those skilled in the art without departing from the spirit and scope of the invention except as it may be limited by the claims.

What is claimed is:

1. A pneumatically-operated gas demand apparatus coupled in interruptible fluid communication between a recipient and at least one source of a pressurized gas and adapted for controlling delivery of the pressurized gas to the recipient as the recipient inhales and exhales, comprising:

a supply valve and a sensing valve cooperable to intermittently deliver pressurized gas to the recipient responsive to the recipient's inhalation and exhalation;

a regulator mechanism including at least one regulator disposed between and in interruptible fluid communication with the at least one source of a pressurized gas and said supply valve; and a control device, said control device including flow control means for controlling flow of pressurized gas from the at least one source of a pressurized gas to said supply valve and flow of pressurized gas from the at least one source of a pressurized gas to said regulator mechanism, said control device further comprising pressure control means for controlling the pressure of pressurized gas discharged by said regulator mechanism.

2. The apparatus of claim 1 wherein said at least one regulator comprises a high pressure regulator and a low pressure regulator.

3. The apparatus of claim 2 wherein said control device comprises means for controlling the pressure of pressurized gas discharged by said low pressure regulator.

4. The apparatus of claim 1 further comprising at least one bolus chamber disposed between and in fluid communication with said at least one regulator and said supply valve.

5. The apparatus of claim 4 wherein said at least one bolus chamber comprises a plurality of bolus chambers.

6. The apparatus of claim 5 where in said plurality of bolus chambers comprises a bolus chamber adapted to accommodate a portion of pressurized gas flow delivered from said at least one regulator, and at least one additional bolus chamber adapter to accommodate at least one additional portion of pressurized gas flow delivered from said at least one regulator.

7. The apparatus of claim 6 wherein said bolus chamber and said at least one additional bolus chamber are connected in series.

8. The apparatus of claim 6 wherein aid bolus chamber and said at least one additional bolus chamber are connected in parallel.

9. The apparatus of claim 6 further comprising:

a supply orifice element having a supply orifice formed therethrough, said supply orifice element being disposed and providing fluid communication between said at least one regulator and said bolus chamber; and at least one additional supply orifice element having a supply orifice formed therethrough, said at least one additional supply orifice element being disposed and providing fluid communication between said at least one regulator and said at least one additional bolus chamber.

10. The apparatus of claim 6 wherein said portion of pressurized gas flow and said at least one additional portion of pressurized gas flow are unequal.

11. The apparatus of claim 6 wherein the ratio of maximum gas flow rate to minimum gas flow rate accommodated by said bolus chamber is about 3:1.

12. The apparatus of claim 6 wherein the ratio of maximum gas flow rate to minimum gas flow rate accommodated by said at least one additional bolus chamber is about 3:1.

13. The apparatus of claim 6 wherein the total gas flow rate accommodated by said bolus chamber and said at least one additional bolus chamber is about 0.5 to about 6 liters per minute.

14. The apparatus of claim 4 wherein said flow control means comprise first flow control means for controlling flow of pressurized gas from the at least one source of a pressurized gas to said supply valve and from the at least one source of a pressurized gas to said regulator mechanism, said means for controlling further comprising second flow control means for controlling flow of pressurized gas from said at least one bolus chamber to said supply valve.

15. The apparatus of claim 1 wherein said control device further comprises a cam plate, said cam plate comprising at least one cam surface for operating said flow control means and another cam surface for operating said pressure control means.

16. The apparatus of claim 14 wherein said control device further comprises a cam plate, said cam plate comprising a first cam surface for operating said first flow control means, a second cam surface for operating said second control means and a third cam surface for operating said pressure control means.

17. A pneumatically-operated gas demand apparatus coupled in interruptible fluid communication between a recipient and at least one source of a pressurized gas and adapted for controlling delivery of the pressurized gas to the recipient as the recipient inhales and exhales, comprising:

a supply valve and a sensing valve cooperable to intermittently deliver pressurized gas to the recipient responsive to the recipient's inhalation and exhalation;

a regulator mechanism including at least one regulator disposed between and in interruptible fluid communication with the at least one source of a pressurized gas and said supply valve; and a control device, said control device including flow control means for controlling flow of pressurized gas from the at least one source of a pressurized gas to said supply valve and flow of pressurized gas from the at least one source of a pressurized gas to said regulator mechanism.

18. A pneumatically-operated gas demand apparatus coupled in interruptible fluid communication between a recipient and at least one source of a pressurized gas and adapted for controlling delivery of the pressurized gas to the recipient as the recipient inhales and exhales, comprising:
- a supply valve and a sensing valve cooperable to intermittently deliver pressurized gas to the recipient responsive to the recipient's inhalation and exhalation;
- a regulator mechanism including at least one regulator disposed between and in interruptible fluid communication with the at least one source of a pressurized gas and said supply valve; and
- a control device, said control device including flow control means for controlling flow of pressurized gas from the at least one source of a pressurized gas to said supply valve, said control device further comprising pressure control means for controlling the pressure of pressurized gas discharged by said regulator mechanism.

19. A pneumatically-operated gas demand apparatus coupled in interruptible fluid communication between a recipient and at least one source of a pressurized gas and adapted for controlling delivery of the pressurized gas to the recipient as the recipient inhales and exhales, comprising:
- a supply valve and a sensing valve cooperable to intermittently deliver pressurized gas to the recipient responsive to the recipient's inhalation and exhalation;
- a regulator mechanism including at least one regulator disposed between and in interruptible fluid communication with the at least one source of a pressurized gas and said supply valve; and
- a control device, said control device including flow control means for controlling flow of pressurized gas from the at least one source of a pressurized gas to said regulator mechanism, said control device further comprising pressure control means for controlling the pressure of pressurized gas discharged by said regulator mechanism.

20. A pneumatically-operated gas demand apparatus coupled in interruptible fluid communication between a recipient and at least one source of a pressurized gas and adapted for controlling delivery of the pressurized gas to the recipient as the recipient inhales and exhales, comprising:
- a supply valve and a sensing valve cooperable to intermittently deliver pressurized gas to the recipient responsive to the recipient's inhalation and exhalation;
- a regulator mechanism including at least one regulator disposed between and in interruptible fluid communication with the at least one source of a pressurized gas and said supply valve;
- cam-operated flow control means for controlling flow of pressurized gas from the at least one source of a pressurized gas to said supply valve and from the at least one source of a pressurized gas to said regulator mechanism; and
- cam-operated pressure control means for controlling the pressure of pressurized gas discharged by said regulator mechanism.

21. The apparatus of claim 20 further comprising at least one bolus chamber disposed between and in fluid communication with said at least one regulator and said supply valve.

22. The apparatus of claim 21 wherein said cam-operated flow control means comprise first cam-operated flow control means for controlling flow of pressurized gas from the at least one source of a pressurized gas to said supply valve and from the at least one source of a pressurized gas to said regulator mechanism, said means for controlling further comprising second cam-operated flow control means for controlling flow of pressurized gas from said at least one bolus chamber to said supply valve.

23. The apparatus of claim 22 further comprising a cam plate, said cam plate comprising a first cam surface for operating said first cam-operated flow-control means, a second cam surface for operating said second cam-operated control means and a third cam surface for operating said cam-operated pressure control means.

24. The apparatus of claim 23 wherein said cam plate is rotatable relative to said cam-operated flow control means and said cam-operated pressure control means.

25. The apparatus of claim 24 further comprising a rotatable knob, said cam plate being operably connected to and driven by said knob.

26. A pneumatically-operated gas demand apparatus coupled in interruptible fluid communication between a recipient and at least one source of a pressurized gas and adapted for controlling delivery of the pressurized gas to the recipient as the recipient inhales and exhales, comprising:
- a supply valve and a sensing valve cooperable to intermittently deliver pressurized gas to the recipient responsive to the recipient's inhalation and exhalation; and
- cam-operated flow control means for controlling flow of pressurized gas from the at least one source of a pressurized gas to said supply valve.

27. A pneumatically-operated gas demand apparatus coupled in interruptible fluid communication between a recipient and at least one source of a pressurized gas and adapted for controlling delivery of the pressurized gas to the recipient as the recipient inhales and exhales, comprising:
- a supply valve and a sensing valve cooperable to intermittently deliver pressurized gas to the recipient responsive to the recipient's inhalation and exhalation;
- a regulator mechanism including at least one regulator disposed between and in interruptible fluid communication with the at least one source of a pressurized gas and said supply valve; and
- cam-operated flow control means for controlling flow of pressurized gas from the at least one source of a pressurized gas to said regulator mechanism.

28. A pneumatically-operated gas demand apparatus coupled in interruptible fluid communication between a recipient and at least one source of a pressurized gas and adapted for controlling delivery of the pressurized gas to the recipient as the recipient inhales and exhales, comprising:
- a supply valve and a sensing valve cooperable to intermittently deliver pressurized gas to the recipient responsive to the recipient's inhalation and exhalation;
- a regulator mechanism including at least one regulator disposed between and in interruptible fluid communication with the at least one source of a pressurized gas and said supply valve; and
- cam-operated pressure control means for controlling the pressure of pressurized gas discharged by said regulator mechanism.

29. In combination with a nebulizer for producing a medicament-containing aerosol and a source of pressurized gas, an intermittent gas delivery device disposed between and in intermittent fluid communication with the nebulizer and the source of pressurized gas, comprising:
- a supply valve and a sensing valve cooperable to intermittently deliver pressurized gas to the recipient responsive to the recipient's inhalation and exhalation;

a regulator mechanism including at least one regulator disposed between and in interruptible communication with the pressurized gas source and said supply valve; and a control device, said control device comprising flow control means for controlling flow of pressurized gas from said pressurized gas source to said supply valve and from said pressurized gas source to said regulator mechanism, said control device further comprising pressure control means for controlling the pressure of pressurized gas discharged by said regulator mechanism.

30. An intermittent gas delivery device according to claim 29 wherein said flow control means and said pressure control means are cam-operated.

31. In combination with a nebulizer for producing a medicament-containing aerosol and a source of pressurized gas, an intermittent gas delivery device disposed between and in intermittent fluid communication with the nebulizer and the source of pressurized gas, comprising:

a supply valve and a sensing valve cooperable to intermittently deliver pressurized gas to the recipient responsive to the recipient's inhalation and exhalation; and cam-operated flow control means for controlling flow of pressurized gas from said pressurized gas source to said supply valve.

32. In combination with a nebulizer for producing a medicament-containing aerosol and a source of pressurized gas, an intermittent gas delivery device disposed between and in intermittent fluid communication with the nebulizer and the source of pressurized gas, comprising:

a supply valve and a sensing valve cooperable to intermittently deliver pressurized gas to the recipient responsive to the recipient's inhalation and exhalation;

a regulator mechanism including at least one regulator disposed between and in interruptible communication with the pressurized gas source and said supply valve; and cam-operated flow control means for controlling flow of pressurized gas from said pressurized gas source to said regulator mechanism.

33. In combination with a nebulizer for producing a medicament-containing aerosol and a source of pressurized gas, an intermittent gas delivery device disposed between and in intermittent fluid communication with the nebulizer and the source of pressurized gas, comprising:

a supply valve and a sensing valve cooperable to intermittently deliver pressurized gas to the recipient responsive to the recipient's inhalation and exhalation;

a regulator mechanism including at least one regulator disposed between and in interruptible communication with the pressurized gas source and said supply valve; and cam-operated pressure control means for controlling the pressure of pressurized gas discharged by said regulator mechanism.

* * * * *